United States Patent [19]

Signorini

[11] Patent Number: 5,038,948

[45] Date of Patent: * Aug. 13, 1991

[54] NURSING APPARATUS

[76] Inventor: Alberto Signorini, Rua Engenheiro Alvaro Niemeyer, 113 Sao Conrado, 22600 Rio de Janeiro, Brazil

[*] Notice: The portion of the term of this patent subsequent to Jun. 4, 2008 has been disclaimed.

[21] Appl. No.: 444,983

[22] Filed: Dec. 4, 1989

Related U.S. Application Data

[63] Continuation-in-part of Ser. No. 345,723, Jun. 2, 1989, abandoned.

[30] Foreign Application Priority Data

Dec. 6, 1988 [BR] Brazil .............................. MU6802634
Dec. 6, 1988 [BR] Brazil .............................. PI8806409

[51] Int. Cl.$^5$ ............................ A61J 9/00; A61J 9/08; A61J 11/04
[52] U.S. Cl. .................................. 215/11.1; 215/11.6; 215/13.1; 215/100 A
[58] Field of Search ................ 215/11.1, 11.6, 100 R, 215/100 A, 13.1, 12.2

[56] References Cited

U.S. PATENT DOCUMENTS

| | | | |
|---|---|---|---|
| 1,375,917 | 4/1921 | LaPaugh | 215/11.6 X |
| 1,428,758 | 9/1922 | Cowles | 215/11.6 |
| 1,510,363 | 9/1924 | Wangen | 215/11.1 |
| 1,637,719 | 8/1927 | Whitlock | 215/11.6 |
| 2,446,451 | 8/1948 | Allen | 215/11.1 |
| 2,448,569 | 7/1948 | Allen | 215/11.1 |
| 2,480,247 | 8/1949 | Jamison et al. | 215/11.6 |
| 2,483,870 | 10/1949 | Bailey | 215/11.6 |
| 2,497,198 | 2/1950 | Allen | 215/11.1 |
| 2,796,062 | 6/1957 | Tupper | 215/11.1 X |
| 2,889,064 | 6/1959 | Kurkjian | 215/11.1 |
| 3,110,407 | 11/1963 | Dahl | 215/100 R X |
| 3,781,360 | 2/1973 | Knutzen | 215/11.6 X |
| 3,990,596 | 11/1976 | Hoftman | 215/11.1 |
| 4,215,785 | 8/1980 | Schwaeger | 215/11.6 |

FOREIGN PATENT DOCUMENTS

| | | | |
|---|---|---|---|
| 492173 | 4/1953 | Canada | 215/11.1 |
| 515466 | 8/1955 | Canada | 215/11.1 |
| 609924 | 8/1926 | France | 215/11.1 |
| 799108 | 6/1936 | France | 215/11.1 |
| 8903204 | 4/1989 | PCT Int'l Appl. | 215/11.1 |

Primary Examiner—Sue A. Weaver
Attorney, Agent, or Firm—Pettis & McDonald

[57] ABSTRACT

A nursing bottle having an unthreaded neck portion to which a nipple is fixed by means of a cap and a counter-cap. Accessories are provided to permit the nursing bottle to have handles and/or an insulation shield.

10 Claims, 3 Drawing Sheets

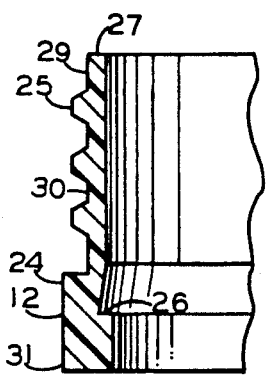
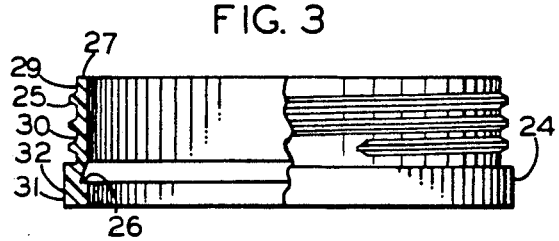
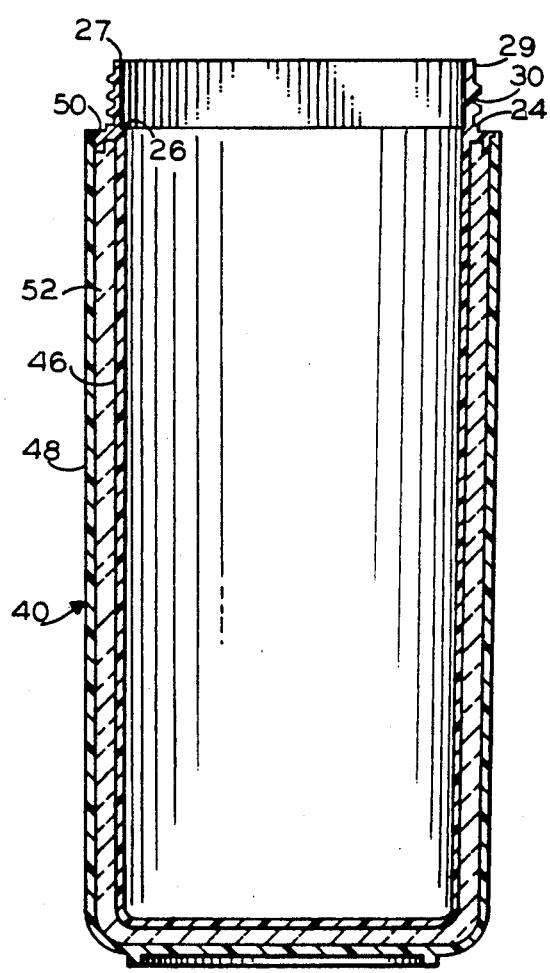
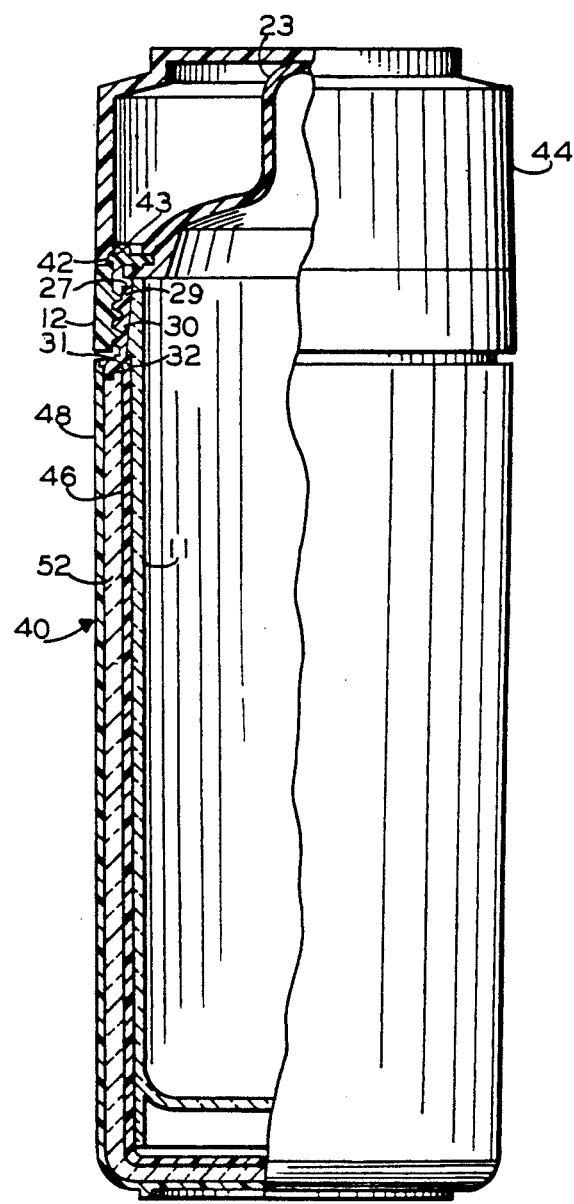
FIG. 3A
FIG. 3
FIG. 4
FIG. 5

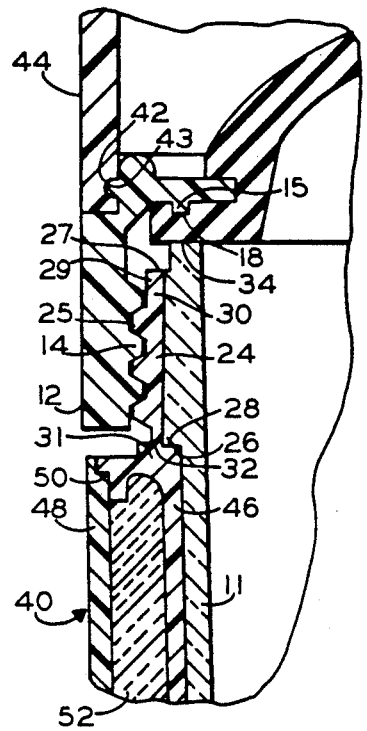
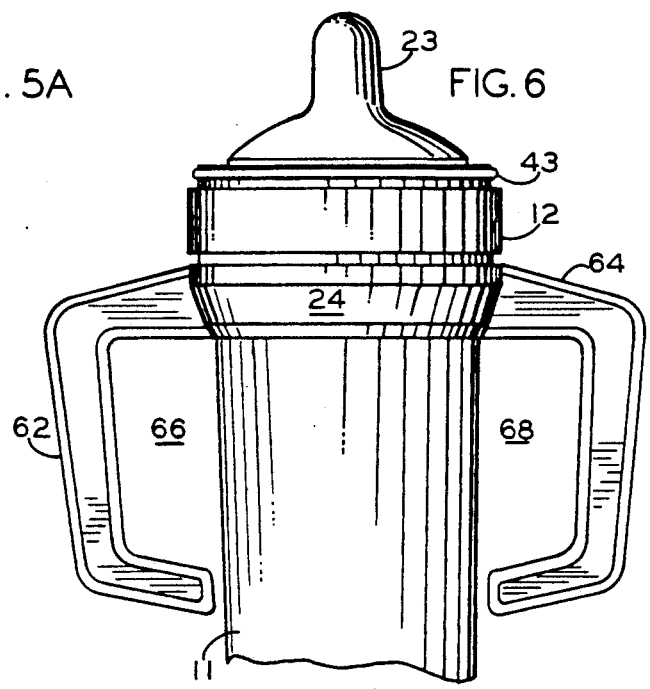
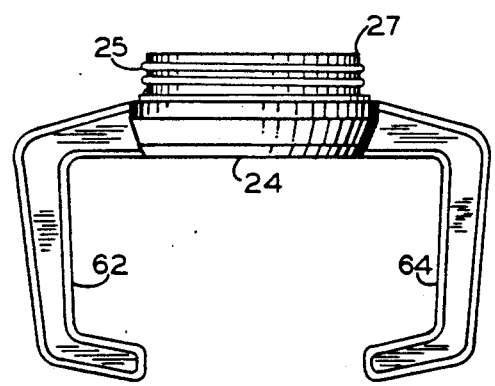
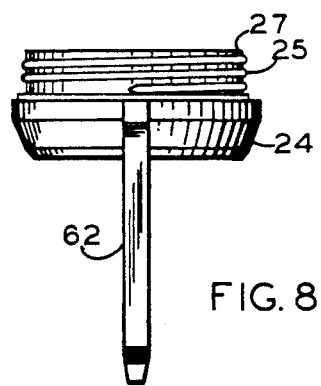
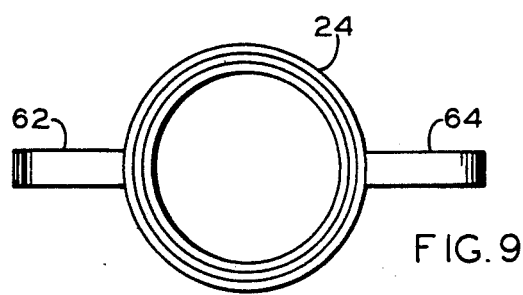
FIG. 5A
FIG. 6
FIG. 7
FIG. 8
FIG. 9

NURSING APPARATUS

This is a continuation-in-part of a co-pending application filed June 2, 1989, Ser. No. 07/345,723, entitled NURSING APPARATUS, now abandoned.

BACKGROUND OF THE INVENTION

Nursing bottles intended for feeding newborns are well known. Basically, such "baby" bottles are formed of a body or flask of different forms which have a threaded neck to which a cap is screwed and to thereby secure a nipple to the neck opening. In many products, an overcap or hood is provided to protect the nipple from outside agents. In general, nursing bottles have not had any major developments in their basic form for many years. The traditional bottle shape has been preserved.

The necks of prior art bottles are generally of standard diameters. The neck is formed by narrowing the body in its upper portion so as to form the characteristic shape of a baby bottle. These bottles have a threaded neck portion and, immediately under the same, an expansion to form the body of the flask. This arrangement can encourage the proliferation of germs and bacteria and makes the bottle difficult to clean. Specifically designed brushes are available for cleaning such bottles. Because of the narrowed neck, dishwashers fail to do a proper job.

The present invention provides a body which, contrary to usual prior art designs, does not have the shape of a bottle but of a glass or cup. The bottle body does not have internal or external threads. It is formed with smooth interior walls and without an abrupt increase or decrease in diameter. This assures a more hygienic container that requires no special brushes to clean. It may be washed with the same ease as a traditional glass.

According to the invention, the nipple-holding cap is not screwed directly on a body or a neck thread. Securement is by a separate counter-cap which is slid upward along the body from the bottom in the direction of the body top edge. The counter-cap engages a stop means that prevents the counter-cap from moving any further upward. The stop means is so located that the counter-cap is maintained in a spaced apart relationship with the first end of the bottle body. By preventing the counter-cap from moving further toward the first end of the bottle body, the counter-cap is retained on the body. When the counter-cap is prevented from twisting the nipple-holding cap may be secured tightly to the first section of the counter-cap, and thus the nipple is attached in fluid flow connection to the first end of the bottle body. However, there is ready removal of the counter-cap with a slight, downward touch.

When the counter-cap is withdrawn, the cap and counter-cap are easily washed and sterilized. When these units are removed, the nursing bottle body is transformed to a classic, smooth-edged, inwardly tapered glass which the child may thereafter use to learn how to drink from a normal drinking glass.

SUMMARY OF THE INVENTION

A principal objective of this invention is to create a novel commercial product which includes an insulated cover for a nursing bottle with a body, or flask, which is smooth, has a wide mouth, and has an inner portion easily accessible for cleaning. The body or flask is constituted of plastic or glass and is wider than the traditional top of a conventional baby bottle. The body tapers slightly inwardly from an upper open end to the closed bottom end. In this respect, the body is an inverted hollow frustum. An insulated cover is adapted for use with this body.

The sealing of the nipple against the body is obtained by pressure between the nipple-holding cap and an insulated counter-cap, the latter being introduced from bottom to top, on the frustum body, and abutting an annular ridge about the body, on the outer surface thereof. This ridge engages a ledge on the interior surface of the counter-cap. The ridge and the ledge acting together, form a stop means that prevents the counter-cap from moving further upward on the body, and thus holds the counter-cap on the body while the counter-cap is being attached to the nipple-holding cap. By tightly fastening the nipple-holding cap to the counter-cap the nipple is brought into sealing contact with the first end of the bottle body. The second section of the counter-cap having the insulated body attached provides insulation.

Another objective is to provide an improvement to a nursing bottle by simply and efficiently providing a thermal insulation for the body which insulation system is isolated from foods contained within the bottle.

A still further objective of the present invention is to provide a double handle which is practical and functional, and which eliminates the inconveniences of cylindrical and smooth nursing bottle bodies used in prior art designs of nursing bottles while preserving the advantages of the instant invention.

These and other objects of the invention will become more apparent to those skilled in the art by reference to the following detailed description when viewed in light of the accompanying drawings.

BRIEF DESCRIPTION OF THE DRAWINGS

FIG. 3 is an elevational view of a counter-cap, partly in section;

FIG. 3A is an enlarged portion of FIG. 3;

FIG. 4 is a front elevational view of another embodiment of the invention, partly in section;

FIG. 5 is a side elevation similar to FIG. 4 with an overcap, nipple-holding cap, and nipple in place;

FIG. 5A is an enlarged portion of FIG. 5;

FIG. 6 is a front elevational view of another embodiment of this invention having handles;

FIG. 7 is a front elevational view of the handle section alone;

FIG. 8 is a side elevation of FIG. 7; and

FIG. 9 is a top plan view of FIG. 7.

DESCRIPTION OF THE PREFERRED EMBODIMENT

Figure 1:
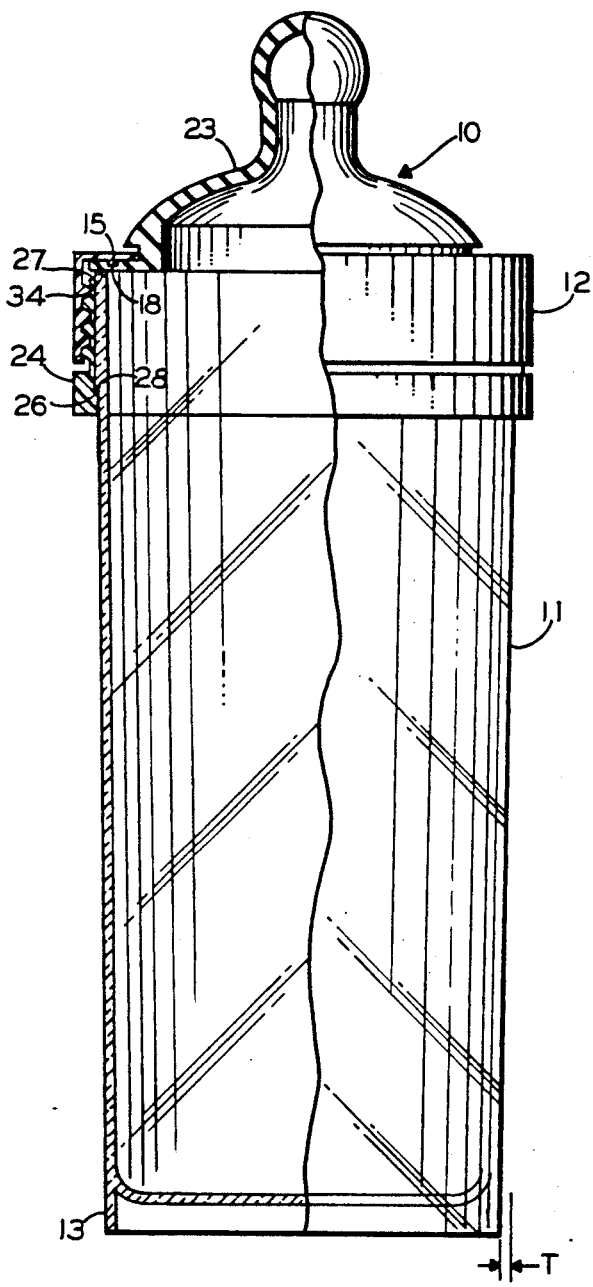
FIG. 1 is a side elevational view, partly in section.
Figure 1A:
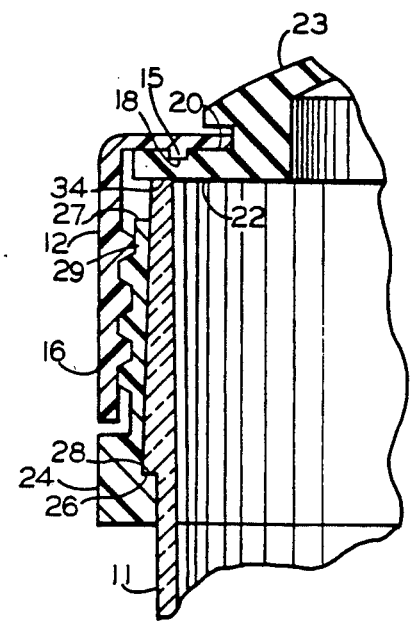
FIG. 1A is an enlarged portion of FIG. 1.
Figure 2:
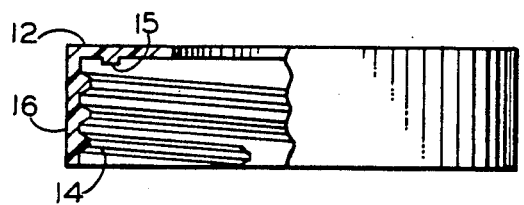
FIG. 2 is an elevational view of a nipple-holding cap member, partly in section.
Figure 2A:
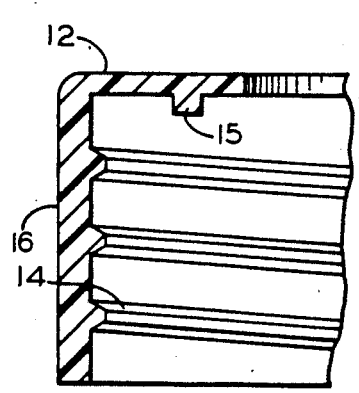
FIG. 2A is an enlarged portion of FIG. 2.

In the following specification, like numerals indicate like parts in all of the figures. FIG. 1 is a partial section of a basic nursing bottle 10 and shows the components assembled. The bottle body 11 of the assembly is tapered from a top edge to the bottom. This taper is depicted by the letter T. FIG. 2 and FIG. 2A disclose a nipple-holding cap 12, with the construction of a thread 14, and further show a tooth 15 that projects downwardly embedding in a circular reception groove 18 formed in the upper surface 20 of the flexible flange 22 of nipple 23. The nipple-holding cap 12 has a downwardly extending skirt 16. FIG. 1A is an enlarged view of the sealing means and includes an enlarged showing of the nipple-holding cap 12, the nipple 23, the body 11, and counter-cap 24.

FIG. 3 and FIG. 3A disclose the counter-cap 24 having a counter-bore forming a ledge 26 which abuts a ridge 28 on the exterior of the upper portion of bottle body 11. The counter-cap 24 has a top surface 27, first end 29 and a second end 31 and a first section 30 and a second section 32, with the ledge 26 interposed between the sections 30 and 32.

FIG. 1A also demonstrates the basic coupling and construction between the nipple-holding cap 12, the counter-cap 24, and the nipple 23 as generally shown in my co-pending application Ser. No. 07/345,723, filed June 2, 1989. The coupling and/or embedding of tooth 15 assures that the flange 22 of nipple 23 is secured between cap 12 and the bottle body 11 so that the nipple 23 is secured to the nursing bottle body. This assures sterility. The sealing of the nipple 23 to body 11 is accomplished by the threading action of threads 14 of nipple-holding cap 12 on the threads 25 of counter-cap 24 together with the embedding of the annular tooth member 15 into the groove 18 of nipple flange 22.

Because of the slight taper T, the counter-cap 24 is easily mounted over the bottom edge 13 of bottle body 11 and slipped upwards until the counter-cap 24 is prevented from moving further by the stop means. The stop means in the preferred embodiment is defined as the annular ridge 28 formed on the exterior of the bottle body 11 and the ledge 26, which is formed interiorly of counter-cap 24, by the counter-bore 26 The ledge 26 of the counter-cap 24 engages the annular ridge 28 preventing further upward movement of the counter-cap 24; however, the counter-cap 24 may be easily removed from the bottle body 11 with a slight, downward touch. The counter-cap 24 can be formed with a slight interior taper which permits the first end 29 of counter-cap 24 to be guided over the ridge. Counter-cap 24 is normally made of plastic with a certain degree of shape memory or elasticity so that the first section 30 can be readily expanded over the ridge, if necessary, so that the ridge 28 is engaged by the ledge. When so positioned, the flange 22 of the nipple is disposed over the top edge 34 of the glass and the nippleholding cap 12 is threadably secured to the counter-cap 24 until the nipple is firmly grasped. The above arrangement permits the use of a relatively smooth, glass-like container having a nipple secured thereto in a sanitary fashion.

As seen in FIGS. 4, 5, and 5A, the basic nursing bottle of FIG. 1 is contained within a thermal holder 40. The unit is closed by a nipple-holding cap 12 and covered by an overcap or hood 44. The thermal holder 40 is comprised of an internal cup 46 and an outer cup 48 made of boilable thermoplastic. The cups 46 and 48 are sealed hermetically at 50. In the space formed between sealing cups 46 and 48, is an efficient thermal insulating material 52, also boilable. The inner cup 46 is formed with a thread as that of the counter-cap 24 shown in FIG. 1.

From a connection point of view, the thermal holder 40 is similar to the counter-cap 24 in the embodiment shown in FIGS. 1 and 2. In fact, the thermal holder 40 connects to and extends downwardly from the second section 32 of counter-cap 24; the thermal holder 40 insulates the bottle body 11. Note that the first section 30 of the counter-cap 24 and a portion of the second section 32 of counter-cap 24 are present and provide the ledge 26 which engages the ridge 28 of the bottle body 11, providing the stop means. The threads 14 of the nipple holding cap 12 are secured to the threads 25 of the first section 30 of the counter-cap 24.

In FIG. 5A, there is shown a protective overcap 44 which is snapped into position against the nipple holding cap 12 by way of a projection 43 and groove 42. This overcap 44 is to protect the nipple from contamination prior to use of the bottle. It is a snap-on protective cap.

FIGS. 6 through 9, inclusive, show another embodiment of the invention. This embodiment provides a handle mechanism for the embodiment shown in FIGS. 1 and 2. However, it can be readily understood that the thermal holder 40 can be equipped with the handle features.

As seen in FIG. 6, a counter-cap 24 is formed with a pair of handles 62 and 64 which are generally U-shaped and provide convenient openings 66 and 68 for the fingers of an infant. The configuration of the counter-cap 24 remains the same as the previously described embodiments.

The described ensemble represents an innovation in the field of nursing bottles of prior art design, characterized by being a simple sterilizable accessory which becomes a part of the nursing bottle without coming into direct contact with the food contained therein.

As shown in FIGS. 4, 5, and 5A, the thermal accessory contains an outer (male) thread upon which the nipple-holding cap of the basic nursing bottle is secured. The overcap 44 contains an indentation 42 in which a projection 43 on the nipple holding cap 12 is lodged. This overcap seals the opening in the nipple, thereby preventing any inconvenient leaking which can occur with traditional nursing bottles. The large chamber of air created by the overcap about the nipple ensures good thermal insulation at the upper end of the nursing bottle.

The ensemble created by using the thermal accessory herein described makes for excellent design. It is compact, simple, and modern. The ensemble can be carried conveniently in traditional tote bags or purses in any position.

FIGS. 6-9, inclusive, disclose the nursing ensemble with the pair of handles 62 and 64. Handles 62 and 64 are designed with dimensions and angles to permit the nursing infant to reach and hold them with natural comfort. The handles are made of thermoplastic materials which are resistant to boiling and are, therefore, sterilizable as in the basic nursing bottle.

In a general manner, while several preferred embodiments of the invention have been disclosed, it should be understood that the invention is not limited to such embodiments as there may be changes made in the arrangement, disposition and location of the parts without departing from the principle of the present invention as comprehended within the scope of the accompanying claims.

I claim:
1. A nursing device comprising
a bottle body comprising a hollow frustrum having an exterior and an interior surface and having first and second ends, said frustrum having a first portion and a second portion, said first end being open and said second end being closed, said second end of said hollow frustrum having a smaller circumference than said first end of said hollow frustrum;

a counter-cap comprising a sleeve having a top surface, exterior and interior surfaces, having a first end and a second end, and having a first section and a second section, said sleeve so sized and configured that said first end of said sleeve may be slidably mounted over said second end of said bottle body such that said sleeve may be slid toward said first end of said bottle body to a stop position, such that said first end of said sleeve is proximal to and spaced apart from said first end of said bottle body;

a stop means located at a predetermined point intermediate said first and said second ends of said bottle body, such that when said counter-cap is mounted on said bottle body, said first end of said counter-cap is held in spaced apart relation from said first end of said bottle body and, said first end of said counter-cap extends upwardly beyond said stop means such that said top surface of said counter-cap is spaced apart from said stop means;

a nipple removably connected to said first end of said bottle body;

a nipple holding cap to which said nipple may be removably mounted, said cap having an interior surface;

an attaching means wherein said nipple holding cap may be removably attached to said counter-cap, such that said nipple is removably sealed in liquid flow relationship to said first end of said bottle body; and at least one handle extending outwardly from said counter-cap, said handle having a first end and a second end, said first end attached to said counter-cap and said second end remaining free.

2. A nursing device as in claim 1, wherein said handle is substantially "U" shaped.

3. A nursing device as in claim 1, wherein each said handle is connected to said second section of said counter-cap.

4. A nursing device as in claim 1 wherein said stop means comprises an annular ridge formed on said exterior surface of said bottle body and an opposing annular ledge formed on the interior surface of the counter-cap, wherein said first portion of said bottle body adjacent said ridge has an exterior circumference greater than the exterior circumference of said second portion of said bottle body adjacent said annular ridge, thus defining said annular ridge interposed therebetween; and wherein said first section of said counter-cap has an interior circumference adjacent said ledge greater than the interior circumference of said second section of said counter-cap adjacent said ledge, thus defining said annular ledge interposed therebetween, said bottle body and said counter-cap so dimensioned that when said first end of said counter-cap is slidably mounted over said second end of said bottle body, said ridge of said counter-cap engages said opposing ledge of said bottle body such that said counter-cap cannot be advanced further.

5. A nursing device comprising:

a bottle body comprising a hollow frustrum having an exterior and an interior surface and having first and second ends, said frustrum having a first portion and a second portion, said first end being open and said second end being closed, said second end of said hollow frustrum having a smaller circumference than said first end of said hollow frustrum;

a counter-cap comprising a sleeve having a top surface, exterior and interior surfaces, having a first end and a second end, and having a first section and a second section, said sleeve so sized and configured that said first end of said sleeve may be slidably mounted over said second end of said bottle body such that said sleeve may be slid toward said first end of said bottle body to a stop position, such that said first end of said sleeve is proximal to and spaced apart from said first end of said bottle body;

a stop means located at a predetermined point intermediate said first and said second ends of said bottle body, such that when said counter-cap is mounted on said bottle body, said first end of said counter-cap is held in spaced apart relation from said first end of said bottle body and, said first end of said counter-cap extends upwardly beyond said stop means such that said top surface of said counter-cap is spaced apart from said stop means;

a nipple removably connected to said first end of said bottle body;

a nipple holding cap to which said nipple may be removably mounted, said cap having an interior surface;

an attaching means wherein said nipple holding cap may be removably attached to said counter-cap, such that said nipple is removably sealed in liquid flow relationship to said first end of said bottle body; and an insulated body having a first end and a second end, having interior and exterior surfaces, the interior surfaces of said insulated body having the same general shape as said exterior of said bottle body, said insulated body being connected to said counter-cap and so sized and configured that when said counter-cap is slidably mounted over said second end of said bottle body, said bottle body is inserted within said insulated body.

6. A nursing device as in claim 5, wherein said insulated body is connected to said second section of said counter-cap.

7. A nursing device as in claim 6, wherein said insulated body further comprises double walls having a space therebetween.

8. A nursing device as in claim 5, wherein said insulated body further comprises at least one handle extending outwardly from said insulated body, said handle having a first end and a second end, said first end attached to said insulated body and said second end remaining free.

9. A nursing device as in claim 8, wherein each said handle is substantially "U" shaped structure, having a base with two ends and two legs, each said leg having a first and a second end, said second end of said legs being angularly attached to a respective end of said base and said first end of one of said legs being attached to said counter-cap and said first end of said other leg remaining free.

10. A nursing device comprising:

a bottle body comprising a hollow frustrum having an exterior and an interior surface and having first and second ends, said frustrum having a first portion and a second portion, said first end being open and said second end being closed, said second end of said hollow frustrum having a smaller circumference than said first end of said hollow frustrum;

a counter-cap comprising a sleeve having exterior and interior surfaces, having a first end and a second end, and having a first section and a second section, said sleeve so sized and configured that said first end of said sleeve may be slidably mounted over said second end of said bottle body such that said sleeve may be slid toward said first end of said bottle body to a stop position, such that said first end of said sleeve is proximal to and spaced apart from said first end of said bottle body;

a stop means located intermediate said first and said second ends of said bottle body, such that when said counter-cap is mounted on said bottle body, said first end of said counter-cap is held in spaced apart relation from said first end of said bottle body;

a nipple removably connected to said first end of said bottle body;

a nipple holding cap to which said nipple may be removably mounted, said cap having an interior surface;

an attaching means wherein said nipple holding cap may be removably attached to said counter-cap, such that said nipple is removably sealed in liquid flow relationship to said first end of said bottle body; and an insulated body comprising double walls, said walls having a space therebetween, said insulated body having a first end and a second end, and having interior and exterior surfaces, the interior surfaces of said insulated body having the same general shape as said exterior of said bottle body, said insulated body being connected to said second section of said counter-cap and so sized and configured that when said counter-cap is slidably mounted over said second end of said bottle body, said bottle body is inserted within said insulated body.

* * * * *